United States Patent [19]

Bartelt et al.

[11] Patent Number: 5,008,478

[45] Date of Patent: Apr. 16, 1991

[54] **AGGREGATION PHEROMONES OF THE NITIDULID BEETLES *CARPOPHILUS HEMIPTERUS*, *CARPOPHILUS LUGUBRIS*, AND *CARPOPHILUS FREEMANI***

[75] Inventors: Robert J. Bartelt, East Peoria; Patrick F. Dowd, Peoria, both of Ill.

[73] Assignee: The United States of America as represented by the Secretary of Agriculture, Washington, D.C.

[21] Appl. No.: 387,555

[22] Filed: Jul. 31, 1989

Related U.S. Application Data

[63] Continuation-in-part of Ser. No. 275,863, Nov. 25, 1988.

[51] Int. Cl.$^5$ ............................................... C07C 9/00
[52] U.S. Cl. ........................................ 585/16; 424/84
[58] Field of Search ............................................ 585/16

[56] References Cited

U.S. PATENT DOCUMENTS

| | | | |
|---|---|---|---|
| 2,842,599 | 7/1958 | Isler et al. | 585/16 |
| 3,284,529 | 11/1966 | Feldman et al. | 585/16 |
| 3,522,321 | 7/1970 | DeYoung | 585/16 |

OTHER PUBLICATIONS

P. R. White et al., "Female Sex Pheromone of the Common Furniture Beetle *Anobium punctatum* (Coleoptera: Anobiidae): Extraction, Identification, and Bioassays," J. Chem. Ecol. 13(7): 1695–1706 (1987).
H. Venkataraman et al., "Total Synthesis of Citreomontanin and Its $C_{18}Z$ Polyene Isomer," Tetrahedron Lett. 28(22): 2455–2458 (1987).
J. M. Smilanick et al., "Attraction of *Carpophilus* spp. (Coleoptera: Nitidulidae) to Volatile Compounds Present in Figs," J. Chem. Ecol. 4(6): 701–707 (1978).
S. R. Alm ewt al., "A Chemical Attractant for *Glischrochilus quadrisignatus* (Coleoptera: Nitidulidae)," J. Econ. Entomol. 78(4): 839–843 (1985).
S. R. Alm et al., "Attraction of *Glischrochilus quadrisignatus* (Coleoptera: Nitidulidae) to Semiochemicals: Butyl Acetate and Propyl Propionate," J. Econ. Entomol. 79(3): 654–658 (1986).

*Primary Examiner*—Curtis R. Davis
*Attorney, Agent, or Firm*—M. Howard Silverstein; Curtis P. Ribando; John D. Fado

[57] ABSTRACT

Male-produced aggregation pheromones were demonstrated in *Carpophilus hemipterus* (L.), *Carpophilus lugubris* Murray, and *Carpophilus freemani* Dobson (Coleoptera: Nitidulidae) using a wind-tunnel bioassay. The attractiveness of the pheromones is greatly enhanced by volatiles from a host plant, and combinations of pheromone and food volatiles typically attract 3–10 times more beetles than either source by itself. The pheromones consist of a series of 12-, 13-, 14-, and 15-carbon unsaturated hydrocarbons. The most abundant of these in *C. hemipterus* is (2E,4E,6E,8E)-3,5,7-trimethyl-2,4,6,8-decatetraene. In *C. lugubris*, the most abundant is (2E,4E,6E,8E)-7-ethyl-3,5-dimethyl-2,4,6,8-undecatetraene, and in *C. freemani*, (2E,4E,6E)-5-ethyl-3-methyl-2,4,6-nonatriene.

5 Claims, No Drawings

AGGREGATION PHEROMONES OF THE NITIDULID BEETLES CARPOPHILUS HEMIPTERUS, CARPOPHILUS LUGUBRIS, AND CARPOPHILUS FREEMANI

CROSS-REFERENCE TO RELATED APPLICATION

This is a continuation-in-part application of Ser. No. 275,863, filed Nov. 25, 1988.

BACKGROUND OF THE INVENTION

1. Field of the Invention

This invention relates to aggregation pheromones of insects, particularly the nitidulid species *Carpophilus hemipterus, C. lugubris,* and *C. freemani,* and the use of these pheromones in combination with host plant volatiles to aid in insect control as, for example, in pheromone-baited traps.

2. References

Throughout this application, various publications are referenced by the name of the author and date of publication within parentheses. Full citations for these references may be found at the end of the specification, listed in alphabetical order.

3. Description of the Prior Art

Insect-produced volatiles (e.g., pheromones) and host plant odors (e.g., kairomones) may facilitate location of conspecifics for mating and orientation to acceptable host plants for feeding and oviposition. It is known that in several, but not all, insect species (e.g., bark beetles) pheromones and a few specific plant odors, such as monoterpenes, may act in synergy, each enhancing the attraction of the other (Borden, 1984).

*Carpophilus hemipterus* (L.) (Coleoptera: Nitidulidae) is a worldwide pest attacking agricultural commodities such as ripe and dried fruit, corn, wheat, oats, rice, beans, nuts, peanuts, cotton seed, copra, spices, sugar, honey, and other materials (Hinton, 1945). It is also able to vector microorganisms responsible for the souring of figs (Hinton, 1945) and fungi which contaminate corn and produce mycotoxins (Wicklow et al., 1988).

The dusky sap beetle, *Carpophilus lugubris* Murray (Coleoptera: Nitidulidae) is distributed from Brazil through Central America (Parsons, 1943) and probably throughout the United States (Sanford, 1958). It is found in ripe and decomposing fruit and vegetables (Sanford and Luckman, 1963), trees infected with oak wilt (Dorsey et al., 1953; Norris, 1953), and poultry manure (Pfeiffer and Axtell, 1980). It is probably most important as a pest of sweet corn (Connell, 1956; Sanford, 1958; Connell, 1975; Tamaki et al., 1982), and can cause large amounts of corn to be rejected at canneries (Luckman and Hibbs, 1959). In addition, it appears to be a vector of oak wilt (Dorsey et al., 1953; Norris, 1953; Appel, 1986), and mycotoxin-producing fungi that contaminate corn (Wicklow et al., 1988). Although tight-husked corn can provide some control, this may be defeated when corn earworms or other insects provide entry holes (Connell, 1956; Tamaki et al., 1982). However, in many cases these insects are able to enter the ears without assistance (Connell, 1956; Tamaki et al., 1982). The loose-husked varieties of dent (field) corn adopted in association with the use of mechanical harvesting promote ready entry sites for these insects (Connell, 1956).

*Carpophilus freemani* Dobson infests sweet corn (Sanford and Luckman, 1963) and corn seed and corn meal (Connell, 1975). It is a principal pest of figs (Smilanick and Ehler, 1976) and the principal vector of *Ceratocystis* canker of stone fruits including almonds, prunes, peaches, and apricots (Moller et al., 1969).

Field traps have been used to monitor or attempt to control these and other nitidulid species, and much research has gone into trap baits. Fermenting fig paste has been used as a trap bait for *C. hemipterus* (Obenauf et al., 1976). Smilanick et al. (1978) determined that a 1:1:1 mixture of acetaldehyde, ethyl acetate, and ethanol was an even more effective bait for *C. hemipterus* than fig paste, but trap catches were still relatively small, given the huge beetle populations. Due to the low activity of 16 other host volatiles tested, Smilanick et al. (1978) concluded that *C. hemipterus* "appears to use a restricted number of olfactory stimuli to locate suitable hosts." Previously reported methods of monitoring *C. lugubris* have been of limited effectiveness. It is well known that these insects can be attracted by fermenting baits (Luckman and Hibbs, 1959). Specific methods include using freshly sawn oak or maple blocks in combination with vinegar and fungi (Neel et al., 1967; Dorsey and Leach, 1956). However, the attractiveness of these baits varies over time due to changes in fermentative activity (Neel et al., 1967). Previously reported methods of attracting *C. freemani* are also of limited effectiveness. The only reported method specifically describing *C. freemani* attraction is that of Smilanick et al. (1978). The response of *C. freemani* to Smilanick's 3-component mixture appeared to be relatively poor compared to that of *C. hemipterus,* and not significantly different from fig paste or controls. Alm et al. (1985, 1986) demonstrated that esters such as propyl propionate and butyl acetate were effective baits for *Glischrochilus quadrisignatus,* another economically important nitidulid, but did not compete with banana. In nature, these chemicals exist in the host plant, are produced by microorganisms which have established on the plants, or both. Curiously, no pheromones have been reported for nitidulid beetles, even though attractants of this type would probably be potent trap baits or additives to presently used baits. Pheromones have been reported for a large number of other beetle species.

SUMMARY OF THE INVENTION

We have now surprisingly found that male-produced aggregation pheromones are secreted by *C. hemipterus, C. lugubris* and *C. freemani.* The attractiveness of the pheromone complexes is greatly enhanced by a range of volatiles from a host food source.

It is an object of this invention to describe the isolation and synthesis of the hydrocarbon components of the aggregation pheromones.

Another object of the invention is to teach an improved method of attracting insects by the combined use of aggregation pheromones and food volatiles.

Other objects and advantages of the invention will become readily apparent from the ensuing description.

DETAILED DESCRIPTION OF THE INVENTION

We have now discovered that male *C. hemipterus, C. lugubris,* and *C. freemani* beetles produce volatile hydrocarbon mixtures which are attractive to both sexes and are, therefore, termed aggregation pheromones. The pheromone complexes are especially effective when used in combination with volatiles from a food source. The isolation, identification, and synthesis of the pheromones and their biological activity, alone and in conjunction with food volatiles, are described below.

It is understood that host food source volatiles may be produced directly by the host plant, by microorganisms such as yeasts which are growing on plant tissues, or by both.

The hydrocarbons of this invention may be represented by the general formula:

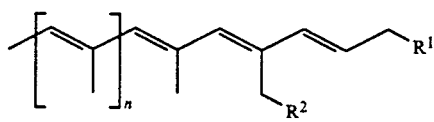

wherein $R^1$ and $R^2$ are independently selected from hydrogen or lower alkyl, and n is zero or one.

The natural and synthetic compounds used in this work are listed below with assigned numbers, which are used in the following text and tables. Structures of the compounds are shown in Table I.

TABLE I
Synthetic Hydrocarbons

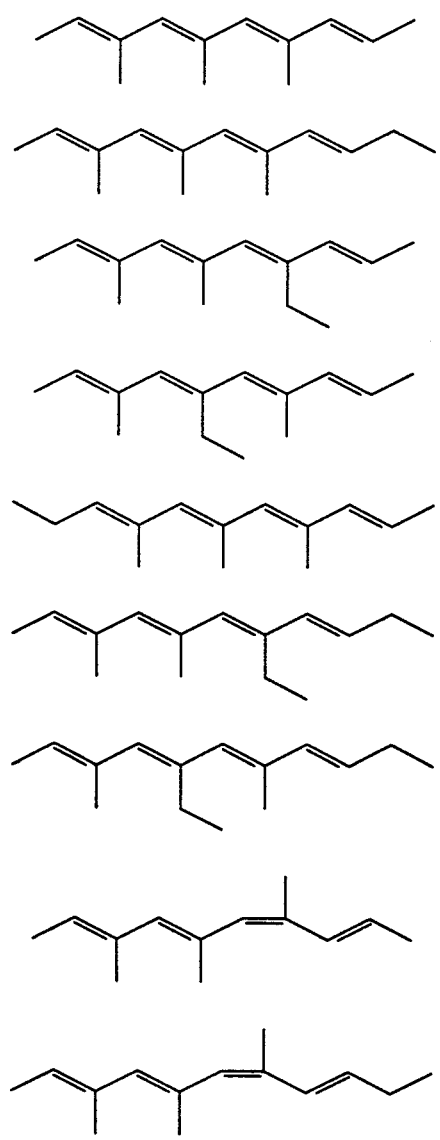

| Compound | Number |
|---|---|
| Compounds found in beetles: | |
| (2E,4E,6E,8E)-3,5,7-Trimethyl-2,4,6,8-decatetraene | 1 |
| (2E,4E,6E,8E)-3,5,7-Trimethyl-2,4,6,8-undecatetraene | 2 |
| (2E,4E,6E,8E)-7-Ethyl-3,5-dimethyl-2,4,6,8-decatetraene | 3 |
| (2E,4E,6E,8E)-5-Ethyl-3,7-dimethyl-2,4,6,8-decatetraene | 4 |
| (2E,4E,6E,8E)-4,6,8-Trimethyl-2,4,6,8-undecatetraene | 5 |
| (2E,4E,6E,8E)-7-Ethyl-3,5-dimethyl-2,4,6,8-undecatetraene | 6 |
| (2E,4E,6E,8E)-5-Ethyl-3,7-dimethyl-2,4,6,8-undecatetraene | 7 |
| (2E,4E,6E)-5-Ethyl-3-methyl-2,4,6-nonatriene | 14 |
| Compounds not found in beetles: | |
| (2E,4E,6Z,8E)-3,5,7-Trimethyl-2,4,6,8-decatetraene | 8 |
| (2E,4E,6Z,8E)-3,5,7-Trimethyl-2,4,6,8-undecatetraene | 9 |
| (4E,6E,8E)-2,3,5,7-Tetramethyl-2,4,6,8-decatetraene | 10 |
| (2E,4E,6E,8E)-3,5,7-Trimethyl-2,4,6,8-dodecatetraene | 11 |
| (2E,4E,6E,8E)-3,5,7,9-Tetramethyl-2,4,6,8-undecatetraene | 12 |
| (2E,4E,6E,8E)-5,7-Diethyl-3-methyl-2,4,6,8-decatetraene | 13 |

SYNTHESIS OF HYDROCARBONS

Compounds 1-14 were prepared as model compounds to aid in structure identification of the natural pheromones and as test materials for the bioassay. Synthetic reactions were performed as described in the literature for similar systems. All reactions, except for the formation of phosphonium salts, were monitored by GC and mass spectrometry. Intermediates were generally used in the subsequent reactions without purification, other than drying over sodium sulfate and removal of solvent. The final step in the synthesis of each tetraene was a Wittig reaction between an aldehyde (Compounds 15-20, Table II) and a phosphonium salt (Compounds 21-27, Table III).

TABLE II
Aldehyde Intermediates

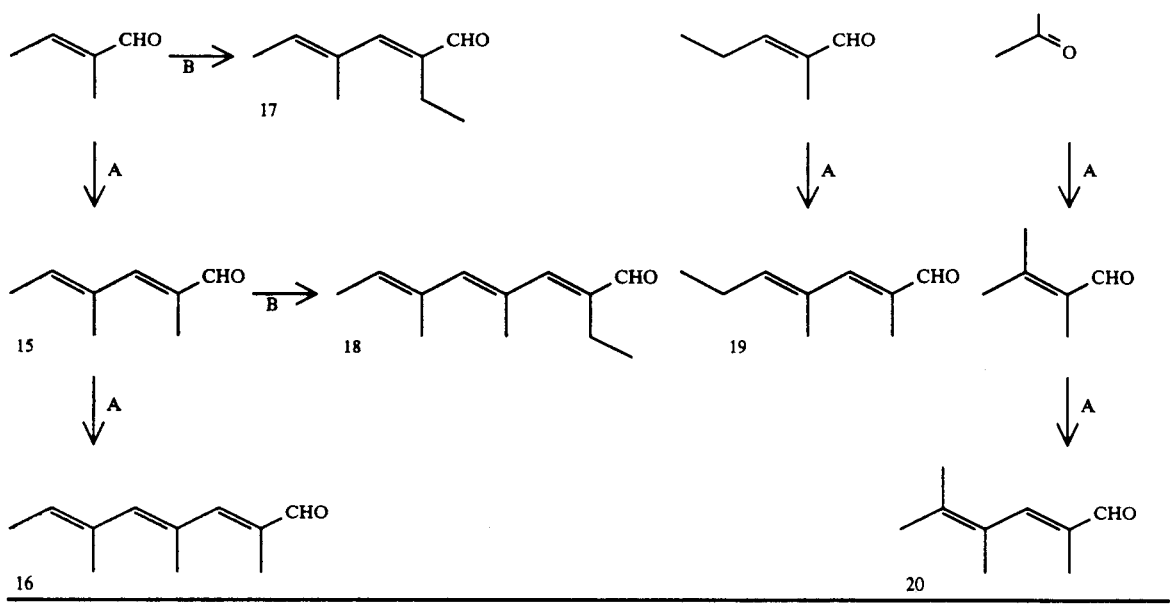

TABLE III
Phosphonium Salt Intermediates

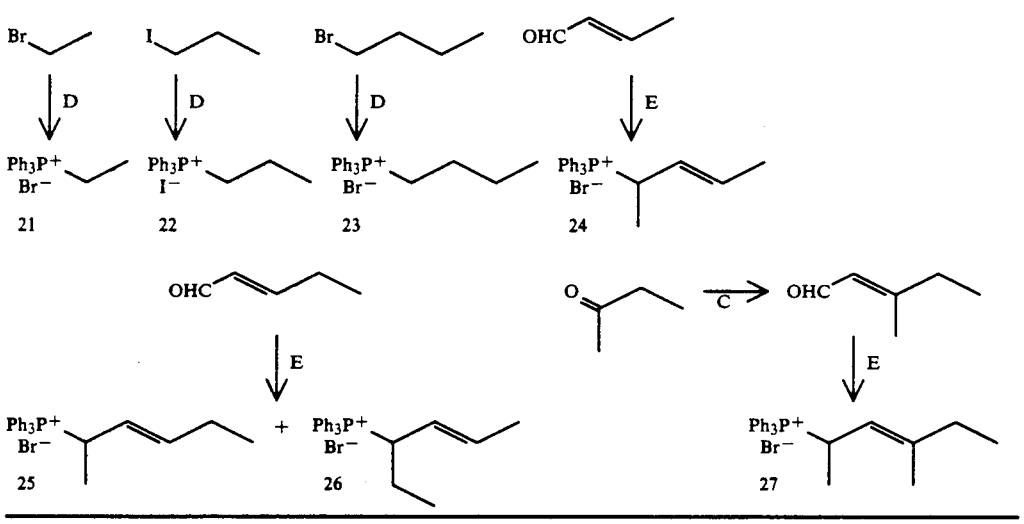

In the synthesis of the aldehyde intermediates (Table II), three commercially available, carbonyl starting materials were used: 2-methyl-2(E)-butenal, 2-methyl-2(E)-pentenal, and acetone. These and subsequent product aldehydes were subjected to two synthetic schemes. In scheme A, the carbonyl starting material was coupled with triethyl 2-phosphonopropionate in a Wittig-Horner condensation, forming an ethyl ester (Gallagher and Webb, 1974). This reaction produces E double bonds stereoselectively (Boutagy and Thomas, 1974). The ester functional group was then reduced to the corresponding alcohol with LiAlH$_4$ as described by Mori (1976) for another ethyl ester, and the alcohol was oxidized with periodinane (Dess and Martin, 1983) to the corresponding aldehyde. These reactions proceeded cleanly, and by capillary GC a single compound usually accounted for over 90% of the volatile reaction products. Scheme B was exactly the same as scheme A except that triethyl 2-phosphonobutyrate was used in the Wittig-Horner reaction. This allowed incorporation of an ethyl side chain into the product instead of a methyl group.

To make the phosphonium salts (Table III), six commercially available starting materials were used: bromoethane, 1-iodopropane, 1-bromobutane, 2(E)-butenal, 2(E)-pentenal, and 2-butanone. These and subsequent intermediates were subjected to three synthetic schemes.

Scheme C was exactly like scheme A except that triethyl 2-phosphonoacetate was used in the Wittig-Horner reaction. This reaction, which was used to link a primary phosphonate anion with a ketone, produced the E and Z isomers in a 60:40 ratio. Fortunately, the desired final tetraene product elaborated from the E intermediate was easily separated chromatographically (AgNO₃-HPLC) from the other isomer.

In scheme D, the alkyl halide was refluxed with triphenylphosphene in acetonitrile for 8 hr, followed by removal of solvent and crystallization of the phosphonium salt trituration under dry ether.

In scheme E, the aldehyde starting material was alkylated with methylmagnesium bromide (Brooks and Snyder, 1955; except that a commercially prepared Grignard reagent was used). Then the alcohol was converted to the bromide with PBr₃ (Noller and Dinsmore, 1943; except that the bromide was recovered by extraction with hexane rather than by distillation). Finally, the secondary, allylic bromide was converted to the phosphonium salt as described for scheme D.

Some allylic rearrangement occurred as the unsaturated salts were formed. Based on analysis of subsequent reaction products, salt 26 represented about 10% of the mixture of 25 and 26. Rearrangement of 24 was not a problem because of symmetry; and allylic rearrangement of 27, if it occurred, was not a problem because the resulting tertiary salt could not take part in a Wittig reaction.

The aldehyde and phosphonium salt intermediates were coupled in a final Wittig reaction as described by Sonnet (1974) to form the desired hydrocarbons (Table IV). With unsaturated phosphonium salts (24–27), the reaction formed both the E and Z isomers of the final double bond in approximately equal proportions. However, with the saturated salts (21-23), the Z isomer was always a minor product (ca. 10%).

The synthetic tetraenes were purified first by column chromatography on silica (hexane as solvent, Example 4). There appeared to be some decomposition on this column (formation of yellow color, which remained on the column), but the expected products were always recovered. Second, the geometrical isomers of the tetraenes were separated by HPLC on the silver-nitrate column (Example 4, 25% or 10% toluene in hexane). It was usually possible to obtain geometrical isomers from this column which, by GC, were not contaminated by the other isomer. Two tetraenes with Z double bonds (8 and 9), were included in bioassay and analytical studies for comparison; but the insect-derived tetraenes were found to have only E double bonds.

Carpophilus hemipterus

The isolation, identification, synthesis, and biological activity of the aggregation pheromones of *C. hemipterus* are described below.

The *C. hemipterus* beetles were reared on a pinto bean diet as described by Dowd (1987). The isolation of the pheromone for this species was guided by a wind-tunnel bioassay (described in detail in Example 1). Briefly, the wind tunnel usually contained 200–400 beetles of mixed sex. Bioassay tests always included two treatments, placed side by side, in the upwind end of the wind tunnel. The beetles located bait materials by flying upwind to the source of the attractive volatiles. The number of beetles landing at each bait was used as a measure of its attractiveness. Simultaneous testing of two treatments made precise comparisons possible, without having to control the numbers of beetles in the wind tunnel or their activity level too closely.

We believe the wind-tunnel bioassay to be more ecologically relevant than the more classical "pit-fall" bioassay used for many stored-product beetles (see Phillips and Burkholder, 1981). The beetles are excellent fliers and, presumably, find and colonize new host sites in the field through flight activity.

One necessary condition for a successful bioassay was that the beetles in the wind tunnel be starved for a number of hours before tests were conducted. When beetles were transferred from their food medium into the wind tunnel, they would quickly form aggregations in the corners and then become motionless. After several hours, a few beetles would begin to move about and take flight spontaneously. This dispersal from the aggregations became more pronounced with time, and responses to pheromone or food baits occurred only after this flight activity had begun. By starving the beetles for 16 hours prior to beginning tests, responses occurred rapidly enough (>10 per 3-min period) to be useful for monitoring pheromone isolation.

The aggregation pheromone could be obtained from the beetles either by extracting whole cultures of the insects (beetles and rearing medium, Example 2) or by collecting volatiles from a culture (Example 3). Initial experiments and synergism studies were conducted with the whole extracts.

The pheromone is produced by male beetles. When an extract of a whole culture containing only males was tested against an equivalent extract derived from females, the beetles in the wind tunnel 1 flew preferentially to that from males. The total bioassay counts were 71 and 1, respectively, over eight 10-min observation periods (ca. 1 beetle equivalent per test). However, both male and female beetles responded readily to the pheromone. In one experiment, the beetles attracted to a culture of males were captured and sexed; of the 142 beetles which responded, 62 were males and 80 were females. The remaining data submitted here represent totals over both sexes.

A methylene chloride extract of whole cultures with males was fractionated on silicic acid; but qualitatively, each of the five fractions was inactive in the bioassay compared with the original extract. However, the recombined fractions were again quite attractive, indicating the active compounds had eluted from the column but that more than one chemical was required for attraction. Collection of volatiles from living beetles (Tenax collection) gave similar results.

It was suspected that both male-derived and diet-derived volatiles were responsible for the activity of the whole cultures. To identify which fraction of the male-derived extract contained the pheromone, we tested combinations of the five chromatographic fractions (described in Example 4). In each combination, one of the fractions was derived from cultures with only males and the remaining four from cultures with only females. Each combination was tested against the whole extract of the female culture (the control in this experiment). Thus, all the bioassay treatments would contain the full complement of diet compounds as well as any "general" metabolites produced by beetles of both sexes and compounds from any associated microorganisms. The attractiveness of the combination of fractions would be expected to differ from the control only if the single male-derived fraction contained the pheromone. From Table V, it is clear that the hexane fraction was the primary source of male-specific attractants. The pheromone was quite nonpolar, indicative of hydrocarbons. Furthermore, only one male-derived fraction was required for potent pheromonal activity. Thus the pheromone appeared not to include components of widely different polarity.

The male-derived attractant was synergized by a wide variety of host volatiles besides those from the rearing medium (Table VI). Effective coattractants included crude plant materials, various yeast cultures, single chemicals (especially esters), and mixtures of chemicals. It is noteworthy that the best previously reported attractant (ethanol, ethyl acetate, and acetaldehyde) attracted over three times more beetles when the pheromone was added to it. Because reproduction in these beetles occurs at feeding sites, the enhanced attraction to combined host- and beetle-derived volatiles is undoubtedly of great ecological importance.

Effective chemical synergists include: (1) $C_1$-$C_4$ straight and branched alcohols; $C_5$ and greater straight chain alcohols. (2) $C_2$ and greater straight and branched acids (except for those which had two methyl groups in the 2 position of the structure). (3) A large number of esters, including: (a) all esters in which both the alcohol and acid moieties are unbranched, especially wherein said moieties are within the range of $C_1$-$C_8$, except for methyl formate, (b) methyl esters with branched acid moieties having no more than 1 methyl branch, and (c) 1-methylethyl acetate and 2-methylpropyl acetate. (4) Aldehydes, ketones, and water. The only bifunctional sample tested, 2-hydroxypropanoic acid, was effective; this more complex compounds could also be synergistic.

TABLE V

Activity of Silica Fractions of Male-Derived Extract in Wind Tunnel

| Male-Derived Fraction | Mean Bioassay Count (n = 6) | |
|---|---|---|
| | Fraction Combination[a] | Control[b] |
| Hexane | 23.3* | 0.5 |
| 5% Ether-hexane | 1.5 | 0.5 |
| 10% Ether-hexane | 1.5 | 1.8 |
| 50% Ether-hexane | 1.2 | 0.8 |
| 10% MeOH—$CH_2Cl_2$ | 2.2 | 1.3 |

[a]Each male-derived fraction was combined with the four complementary fractions derived from females. The only significantly active combination is marked with an (*).
[b]The control for this experiment was the whole extract of a culture of females. Therefore, each bait in the experiment contained all the same diet-derived compounds, as well as any compounds shared by both sexes of beetles.

TABLE VI

Synergistic Interactions Between Host Plant Volatiles and Pheromones of Carpophilus hemipterus

| Volatile | Mean bioassay count (n > = 8) | | |
|---|---|---|---|
| | Volatile | Pheromone | Volatile + Pheromone |
| Crude Host Materials | | | |
| Orange juice | 0.5 a | 1.0 a | 10.6 b |

TABLE VI-continued
Synergistic Interactions Between Host Plant Volatiles and Pheromones of *Carpophilus hemipterus*

| | Mean bioassay count (n> = 8) | | |
|---|---|---|---|
| Volatile | Volatile | Pheromone | Volatile + Pheromone |
| Apple juice | 1.2 a | 1.3 a | 15.6 b |
| Juice of corn kernels | 0.1 a | 2.4 b | 6.3 c |
| Corn silk | 0.0 a | 4.5 b | 8.8 c |
| Corn husk | 0.0 a | 2.8 b | 8.2 c |
| Corn kernel | 0.0 a | 2.5 b | 13.2 c |
| Corn kernel + silk | 0.5 a | 3.0 b | 21.0 c |
| Baker's yeast on agar medium | 0.4 a | 1.9 a | 6.3 b |
| Baker's yeast on banana | 2.2 a | 3.5 a | 30.4 b |
| Z.b. on banana | 3.2 a | 3.0 a | 24.8 b |
| Esters | | | |
| Methyl formate | 1.7 a | 16.2 b | 18.9 b |
| Methyl acetate | 1.5 a | 6.1 b | 21.3 c |
| Methyl propanoate | 6.4 a | 6.4 a | 43.5 b |
| Methyl butanoate | 8.6 a | 3.1 b | 41.7 c |
| Methyl 2-methylpropanoate | 0.9 a | 2.4 b | 15.5 c |
| Methyl pentanoate | 1.2 a | 6.1 b | 25.8 c |
| Methyl 2-methylbutanoate | 2.1 a | 6.5 b | 30.4 c |
| Methyl 3-methylbutanoate | 0.0 a | 8.1 b | 13.5 c |
| Methyl 2,2-dimethylpropanoate | 0.3 a | 2.9 b | 4.5 b |
| Methyl 4-methylpentanoate | 0.7 a | 6.5 b | 21.5 c |
| Ethyl acetate | 0.3 a | 2.9 b | 14.7 c |
| Ethyl propanoate | 1.4 a | 5.2 b | 35.9 c |
| Ethyl butanoate | 0.3 a | 2.4 b | 18.7 c |
| Ethyl 2-methylpropanoate | 0.1 a | 1.3 b | 3.2 b |
| Ethyl 3-methylbutanoate | 0.3 a | 5.0 b | 4.0 b |
| Propyl acetate | 1.0 a | 2.6 a | 17.2 b |
| 1-Methylethyl acetate | 1.4 a | 7.0 b | 25.4 c |
| Propyl propanoate | 2.5 a | 2.5 a | 72.0 b |
| Butyl acetate | 0.1 a | 2.7 b | 10.6 c |
| 2-Methylpropyl acetate | 0.0 a | 2.4 b | 8.6 c |
| 1-Methylpropyl acetate | 0.2 a | 2.3 b | 3.6 b |
| 1,1-Dimethylethyl acetate | 0.0 a | 2.4 b | 1.2 b |
| Butyl propanoate | 0.0 a | 10.0 b | 34.0 c |
| Pentyl acetate | 1.7 a | 3.0 a | 14.3 b |
| 1-Methylbutyl acetate | 0.9 a | 6.0 b | 9.4 b |
| 2-Methylbutyl acetate | 0.0 a | 5.3 b | 2.7 b |
| 3-Methylbutyl acetate | 0.4 a | 5.2 b | 6.4 b |
| 1-Ethylpropyl acetate | 0.3 a | 6.0 b | 3.8 b |
| Heptyl hexanoate | 0.4 a | 1.0 b | 8.3 c |
| Octyl acetate | 0.4 a | 2.6 b | 13.9 c |
| Benzyl acetate | 0.1 a | 0.7 ab | 1.8 b |
| Alcohols | | | |
| Methanol | 3.1 a | 1.9 a | 13.9 b |
| Ethanol | 1.3 a | 3.1 a | 16.3 b |
| 1-Propanol | 4.4 a | 14.9 b | 61.0 c |
| 2-Propanol | 6.6 a | 8.7 a | 41.0 b |
| 1-Butanol | 0.1 a | 2.6 b | 8.0 c |
| 2-Methyl-1-propanol | 0.2 a | 33.8 b | 24.5 b |
| 1,1-Dimethylethanol | 1.5 a | 7.8 b | 32.9 c |
| 2-Butanol | 0.4 a | 7.1 b | 17.8 c |
| 2-Methyl-1-butanol | 0.2 a | 4.7 b | 3.3 b |
| 3-Methyl-1-butanol | 1.2 a | 15.8 b | 11.5 b |
| 1-Heptanol | 0.2 a | 1.6 b | 5.5 c |
| Acids | | | |
| Formic acid | 0.1 a | 1.2 b | 1.7 b |
| Acetic acid | 0.3 a | 3.0 b | 8.7 c |
| Propanoic acid | 6.7 a | 8.9 a | 74.4 b |
| 2-Hydroxypropanoic acid | 0.6 a | 2.5 a | 8.7 b |
| Butanoic acid | 0.4 a | 3.0 b | 19.3 c |
| 2-Methylpropanoic acid | 0.2 a | 10.2 b | 7.1 b |
| Pentanoic acid | 1.5 a | 5.9 b | 25.8 c |
| 2-Methylbutanoic acid | 4.3 a | 3.6 a | 34.1 b |
| 3-Methylbutanoic acid | 0.9 a | 7.2 b | 21.0 c |
| 2,2-Dimethylpropanoic acid | 0.1 a | 6.6 b | 6.4 b |
| 3-Methylpentanoic acid | 3.0 a | 5.8 b | 30.0 c |
| 4-Methylpentanoic acid | 2.7 a | 3.7 b | 24.2 c |
| 2,2-Dimethylbutanoic acid | 0.1 a | 11.4 b | 15.6 b |
| Other Single Components | | | |
| Acetaldehyde | 0.0 a | 2.4 b | 7.8 c |
| Propanal | 2.4 a | 0.8 b | 7.0 c |
| 2-Pentanone | 0.2 a | 0.8 a | 7.7 b |
| Water | 0.2 a | 6.1 b | 10.4 c |
| Mixtures (all 1:1:1) | | | |
| Ethanol:acetaldehyde: ethyl acetate | 9.2 a | 4.5 b | 29.6 c |
| Ethanol:ethyl butanoate: | 2.1 a | 2.2 a | 32.4 b |

TABLE VI-continued

Synergistic Interactions Between Host Plant
Volatiles and Pheromones of *Carpophilus hemipterus*

| Volatile | Mean bioassay count (n ≥ = 8) | | |
|---|---|---|---|
| | Volatile | Pheromone | Volatile + Pheromone |
| 2-hydroxypropanoic acid | | | |
| Ethanol:ethyl propanoate: propanoic acid | 8.9 a | 5.0 b | 43.9 c |
| Ethanol:ethyl propanoate: acetaldehyde | 6.6 a | 3.9 b | 28.2 c |
| Ethanol:ethyl 2-methylpropanoate: 2-hydroxypropanoic acid | 2.0 a | 5.3 b | 16.1 c |

Each line represents one experiment; data are mean counts per 3-min test. In each line, means followed by the same letter are not significantly different (LSD, P = 0.05). Baker's yeast = *Saccharomyces cerevisiae;* the agar medium was potato dextrose agar. Z.b. = *Zygosaccharomyces bailii.* The pheromone source was the hydrocarbon fraction of an extract derived from a whole culture containing male beetles; the concentration was adjusted so that there was 0.5–1.0 ng of the major pheromone component per test; in each line of the table the amount of pheromone used was constant.

The active compound from the male beetles appeared to have at least one double bond, because the 10% ether-hexane fraction from the AgNO$_3$ column contained most of the activity (Table VII). A hydrocarbon without double bonds would have eluted with hexane. Further purification by HPLC with the size-exclusion column yielded two consecutive 1-ml fractions that were quite active (Table VII). The size-exclusion column was very valuable for separating inert hydrocarbons of high molecular weight from the attractants. Male-derived Tenax collections also provided active hydrocarbons, and these were fractionated by HPLC on the AgNO$_3$ column. Four consecutive 0.5-ml fractions had activity (Table VII). As with the open column, the retention of active fractions indicated unsaturation in the pheromone.

Parallel chromatographic fractions derived from female beetles were prepared, and the fractions from both sexes were analyzed by GC. In the active, male-derived HPLC fractions there were at least 11 compounds that were absent from the females (Table VIII). Considering both the GC and bioassay data, it was clear that no single compound was absolutely required for activity and that more than one subset of male-specific hydrocarbons was sufficient to elicit attraction. However, complete separation of these compounds was not obtained by any HPLC method. Preparative GC did not provide pure compounds either, because many were too similar in GC retention and too labile to survive this technique.

In the extracts of male cultures, 1 beetle equivalent contained approximately 1 ng of the major component (I=13.83, Table VIII). In a typical Tenax collection, 1 beetle-day represented ca. 0.5 ng of this component. Because the beetles could live for several months in the aeration flasks, the Tenax collections were the richer source of active hydrocarbons and, furthermore, these were relatively easy to purify.

TABLE VII

Activity of Chromatographic Fractions Derived
from Male *C. hemipterus* Hydrocarbons[a]

| | Mean Bioassay Count (n = 4) | |
|---|---|---|
| Fraction Description | Fraction + Coattractant[b] | Coattractant[b] |
| AgNO$_3$ fractions (open column, from culture extract) | | |
| Hexane | 1.0 | 1.3 |
| 5% Ether-hexane | 15.0* | 2.0 |
| 10% Ether-hexane | 33.3* | 1.3 |
| 25% Ether-hexane | 6.7 | 2.5 |
| Ether (first) | 1.3 | 2.0 |
| Ether (second) | 0.8 | 1.0 |
| Size-exclusion fractions (HPLC, from AgNO$_3$ 10% ether-hexane fraction, above) | | |
| 8–10 ml after injection | 0.8 | 1.0 |
| 10–11 ml | 12.0* | 1.5 |
| 11–12 ml | 9.3* | 1.0 |
| 12–13 ml | 3.0 | 1.0 |
| 13–14 ml | 1.0 | 1.8 |
| 14–15 ml | 1.0 | 1.3 |
| 15–16 ml | 1.5 | 1.0 |
| AgNO$_3$ fractions (HPLC, from Tenax collections) | | |
| 3.0–4.5 ml after injection | 0.0 | 0.3 |
| 4.5–5.0 ml | 0.0 | 0.0 |
| 5.0–5.5 ml | 0.5 | 0.0 |
| 5.5–6.0 ml | 12.8* | 0.3 |
| 6.0–6.5 ml | 12.0* | 0.0 |
| 6.5–7.0 ml | 25.8* | 0.8 |
| 7.0–7.5 ml | 4.8* | 0.3 |
| 7.5–8.0 ml | 0.8 | 0.3 |

[a]Hydrocarbons were isolated by column chromatography on silica prior to separations listed in Table. The symbol "*" denotes a statistically significant (P < 0.05) difference from the control.
[b]In first two data sets, coattractant was the extract from female beetles + diet; in the last experiment, coattractant was propyl acetate (10% in mineral oil, 10 μl per test.)

TABLE VIII

Male-Specific Hydrocarbons in *C. hemipterus*

| Retention Index (I)[a] | Relative Amount | Molecular Weight | HPLC Retention (ml)[b] | | Structure No. |
|---|---|---|---|---|---|
| | | | Size Exclusion | AgNO$_3$ | |
| 12.44 | 3% | 176 | (not detected) | 6.0–6.5*[c] | — |
| 13.08[d] | 11% | 176 | 10.5–11.5* | 6.0–6.5* | — |
| 13.29[d] | 4% | 176 | 11.0–12.0* | 5.0–5.5 | — |
| 13.83 | 57% | 176 | 11.0–12.0* | 6.5–7.5* | 1 |
| 14.22 | 4% | 190 | 10.0–11.0* | 5.5–6.5* | 4 |
| 14.28 | 3% | 190 | 10.5–11.5* | 5.5–6.5* | 3 |
| 14.63 | 7% | 190 | 10.5–11.5* | 6.5–7.0* | 5 |
| 14.76 | 8% | 190 | 11.0–12.0* | 6.0–7.0* | 2 |
| 14.91 | 1% | 204 | 10.0–11.0* | 6.0–6.5* | — |
| 15.13 | 0.4% | 204 | (not detected) | 5.5–6.0* | 7 |

TABLE VIII-continued

Male-Specific Hydrocarbons in *C. hemipterus*

| Retention Index (I)[a] | Relative Amount | Molecular Weight | HPLC Retention (ml)[b] | | Structure No. |
|---|---|---|---|---|---|
| | | | Size Exclusion | AgNO$_3$ | |
| 15.15 | 2% | 204 | 10.0–11.0* | 5.5–6.0* | 6 |

[a]Retention index relative to n-alkanes; determined from temperature programmed runs (10°/min) by linear interpolation.
[b]Based on examination of fractions by GC. Many retention volumes represent two consecutive HPLC fractions which both contained the compound.
[c]*indicates that HPLC fraction was active in bioassay.
[d]Also appears in every fraction where the major hydrocarbon (I = 13.83) occurs; these may be decomposition products.

Mass spectra of the unknown compounds were obtained (Example 5). The EI mass spectrum of the most abundant compound suggested the molecular weight to be 176. This was confirmed by the CI mass spectrum, in which the major peaks were 177 (M+1) and 233 (M+57, due to the isobutane reagent gas). The molecular weight is consistent with the molecular formula $C_{13}H_{20}$, indicating four double-bond equivalents. There was no evidence for oxygen or other heteroatoms in the mass spectrum. All fragment ions had reasonable $C_XH_Y$ formulae, and the chromatographic evidence favored a hydrocarbon also. The other male-specific peaks had similar mass spectra, indicating hydrocarbons of 13, 14, or 15 carbons, all with four double-bond equivalents (Table VIII). Based on hydrogenation studies, mass spectra, ultraviolet spectra, and NMR spectra, it was evident that the most abundant pheromone component of *C. hemipterus* (I=13.83) was structure 1. This structure was confirmed by synthesis. Two synthetic methods were used so that there was no ambiguity about the configurations of the double bonds. (All double bonds were either present in the geometrically pure starting materials or were formed stereoselectively by known reactions). The synthetic compound matched the natural pheromone component in all respects: NMR spectrum, mass spectrum, mass spectra of hydrogenation products, UV spectrum, HPLC retentions on size-exclusion and AgNO$_3$ columns, and GC retentions of hydrogenation products.

Six minor components present in the male beetles (compounds 2–7) were identified by the preparation of model compounds which matched the natural compounds exactly. Synthetic targets were chosen based on chromatographic retentions and mass spectral fragmentation patterns of the natural compounds and their hydrogenated derivatives. Synthetic compounds were produced which were identical to the natural ones in GC and HPLC retentions, mass spectra, mass spectra of hydrogenated derivatives, and GC retentions of hydrogenated derivatives. The synthetic compounds (1-14) differed substantially in chromatographic and spectral properties; thus the analytical methods used were sufficiently sensitive to discriminate among these similar structures. There was not enough of any minor component to obtain an NMR spectrum, nor could pure 7 be isolated from the beetles in large enough quantities for hydrogenation to be possible. NMR spectra were obtained for the synthetic compounds to confirm that the target structures were indeed produced.

A mixture of the tetraenes was prepared to mimic the natural pheromone as closely as possible (Table IX). This blend was comparable in activity to the natural pheromone (Table X), and both treatments were very active compared with the control. In addition to the identified tetraenes, the beetle-derived collection contained (by GC) low levels of still unidentified tetraenes and compounds derived from the beetle diet that were not separated from the active constituents during sample preparation. From the bioassay data, these additional compounds appeared to be biologically inert. Therefore, the mixture of the synthesized tetraenes, or a subset of these, was sufficient to account for the activity of the pheromone.

Individually, and at the same doses as in the whole mixture, only two of the seven synthetic tetraenes were significantly above control levels in the bioassay (Table XI). These were the $C_{14}$- component, (2E,4E,6E,8E)-3,5,7-trimethyl-2,4,6,8-undecatetraene (2), and the $C_{13}$ major component, (2E,4E,6E,8E)-3,5,7-trimethyl-2,4,6,8-decatetraene (1), which had 27% and 11% of the activity of the whole mixture, respectively.

TABLE IX

Composition of Bioassay Mixtures, Based on Analysis by GC

| Structure Number | Retention Index (GC) | Pheromone Sample from *C. hemipterus* (pg/10 µl) | Synthetic Mixture (pg/10 µl) |
|---|---|---|---|
| 1 | 13.83 | 1000 | 1000 |
| 2 | 14.76 | 130 | 135 |
| 3 | 14.28 | 80 | 76 |
| 4 | 14.22 | 33 | 39 |
| 5 | 14.63 | 59 | 64 |
| 6 | 15.15 | 19 | 23 |
| 7 | 15.13 | 3 | 6 |

TABLE X

Bioassay Comparison of Pheromone Derived from *C. hemipterus* and Synthetic Tetraene Mixture

| Treatment | Mean Bioassay Count (n = 24) |
|---|---|
| Beetle-derived pheromone + propyl acetate | 13.7 a |
| Synthetic tetraene mixture + propyl acetate | 14.8 a |
| Propyl acetate (experimental control) | 0.3 b |

Beetle-derived and synthetic preparations described in Table III; 10 µl of each solution used per test.

TABLE XI

*C. hemipterus*: Bioassay of Individual Tetraenes at the Same Dose as in the Synthetic Mixture

| Structure Number | Dose (pg) | Activity Index | Mean Bioassay Counts (n = 8) | | |
|---|---|---|---|---|---|
| | | | Tetraene | Synthetic Mix | Control |
| 2 | 130 | 27% | 6.9*** | 20.4 | 1.8 |
| 1 | 1000 | 11% | 2.0*** | 16.2 | 0.3 |
| 3 | 80 | 4% | 1.1 | 20.5 | 0.4 |
| 6 | 19 | 2% | 0.6 | 20.4 | 0.2 |
| 4 | 33 | 2% | 0.7 | 14.2 | 0.5 |
| 5 | 59 | −2% | 0.2 | 13.2 | 0.4 |

TABLE XI-continued

*C. hemipterus*: Bioassay of Individual Tetraenes at the Same Dose as in the Synthetic Mixture

| Structure Number | Dose (pg) | Activity Index | Mean Bioassay Counts (n = 8) | | |
|---|---|---|---|---|---|
| | | | Tetraene | Synthetic Mix | Control |
| 7 | 3 | −2% | 0.5 | 21.4 | 0.9 |

All bioassay treatments, including the control, also contain the synergist, propyl acetate (10 μl of a 10% solution in mineral oil). Each line represents a balanced incomplete block experiment. Significant difference between tetraene and control indicated by *** (P < 0.001). Activity index = 100 × (tetraene − control)/(synthetic mix − control). The activity index expresses the activity of a tetraene as a percent of the activity of the synthetic mixture, correcting for controls.

TABLE XII

*C. hemipterus*: Bioassay of Synthetic Tetraenes, All at 1.3 ng Total Tetraene Per Test

| Structure Number | Activity Index | Mean Bioassay Count (n = 8) | | |
|---|---|---|---|---|
| | | Tetraene | Synthetic Mixture | Control |
| 2 | 52% | 8.9*** | 16.2 | 1.0 |
| 6 | 47% | 5.9*** | 12.3 | 0.3 |
| 3 | 20% | 3.3*** | 14.7 | 0.6 |
| 1 | 10% | 1.9*** | 15.4 | 0.4 |
| 11 | 7% | 1.7** | 17.0 | 0.5 |
| 8 | 5% | 1.4 | 13.4 | 0.8 |
| 13 | 3% | 1.6 | 17.9 | 1.0 |
| 7 | 3% | 0.9 | 15.4 | 0.4 |
| 12 | 3% | 0.8 | 10.9 | 0.4 |
| 5 | 3% | 0.8 | 12.9 | 0.4 |
| 9 | 3% | 1.8 | 12.5 | 1.5 |
| 10 | 2% | 0.8 | 12.0 | 0.6 |
| 4 | 1% | 0.5 | 10.9 | 0.3 |

Experimental design and definition of terms as in Table XI. Significant differences between tetraenes and controls indicated by  (P < 0.01) and * (P < 0.001). Again, all treatments contained propyl acetate in addition to the compounds indicated. Synthetic mixture (see Table IX) used at 1.3 ng per test.

These components were retested, along with other synthetic tetraenes, at a higher dose (1.3 ng test), so that these had the same total ng of tetraene as the synthetic mixtures (Table XII). Two more of the individual natural tetraenes now showed significant activity: These were the 7-ethyl-$C_{15}$ component (structure 6) and the 7-ethyl-$C_{14}$ component (structure 3), with 47% and 20% of the activity of the synthetic mixture, respectively. The most active $C_{14}$ component (structure 2) also showed ca. 2-fold increase in activity in this experiment, due to the 10-fold increase in dose. Neither of the natural tetraenes with an ethyl group at the 5 position (structures 4 and 7) was active at any dose, nor was (2E,4E,-6E,8E)-4,6,8-trimethyl-2,4,6,8-undecatetraene (structure 5).

Of the tested tetraenes that did not occur in the beetles, only one was marginally active. (2E,4E,6E,8E)-3,5,7-Trimethyl-2,4,6,8-dodecatetraene (structure 11) was 7% as active as the synthetic mixture, on an equal weight basis.

Thus, by virtue of their relatively high natural amounts and significant activity, it appeared that the major $C_{13}$ and most active $C_{14}$ components (structures 1 and 2) were the compounds of primary biological importance; but two additional compounds, the 7-ethyl-$C_{14}$ and $C_{15}$ components (structures 3 and 6) showed activity when tested at 20–50 times the original level. A combination of 1 and 2, at the levels shown in Table IX, was equivalent in activity to the whole synthetic mixture (mean counts were 15.2 and 15.9, respectively, n=24, P=0.50, paired t test).

The four natural components that showed activity alone were tested again, in binary combinations, for evidence of synergistic activity (Table XIII). The most abundant natural component (1) was used at 1 ng/test; the other (2, 3, and 6) were used at 250 pg/test. Counts for three binary mixtures were quite low (lines 2, 5, and 6 of Table XIII), despite the observation that the beetles in the wind tunnel had responded readily to the standard synthetic mixture before and after the experiments were conducted. On the other hand, the binary combinations 1+2, 1+6, and 2+3 provided good counts consistently. When all six binary mixtures were tested against the whole synthetic mixture and the control, only the mixture 1+3 performed poorly (Table XIV).

TABLE XIII

*C. hemipterus*: Bioassay Activity of Six Binary Mixtures of Tetraenes and the Individual Components - Mean Bioassay Counts (n = 6)

| Control | Individual Components (by Structure No.) | | | | Binary Mixture |
|---|---|---|---|---|---|
| | 1 | 2 | 3 | 6 | |
| 0.7 d | 2.5 c | 9.1 b | — | — | 15.5 a |
| 0.6 b | 5.2 a | — | 1.1 b | — | 3.4 a |
| 1.3 c | 2.2 bc | — | — | 3.4 b | 11.1 a |
| 0.8 c | — | 11.1 a | 4.0 b | — | 14.4 a |
| 0.4 b | — | 2.7 a | — | 1.8 a | 3.5 a |
| 0.0 b | — | — | 1.0 b | 0.8 b | 4.5 a |

Each line represents a balanced incomplete block experiment (4 treatments, tested 2 at a time). All treatments contained the synergist, propyl acetate. The $C_{13}$ tetraene (1) was used at 1.0 ng per test; the other tetraenes (2, 3, and 6) were used at 250 pg per test. In each row, means followed by the same letter were not significantly different (P < 0.05, LSD method).

The interactions of pheromone components are complex, and interpretation of wind tunnel data for certain mixtures is difficult. Nevertheless, the combination of 1 and 2 was always effective in the tests, and the beetles responded clearly to 3 and 6 in many instances. It is concluded that 1, 2, 3, and 6 are the most biologically important male-derived pheromone components.

*C. lugubris*

*C. lugubris* beetles were field collected in oak woods and corn fields near Bath, Ill., by attracting them to traps each baited with individual cups of fermenting whole wheat dough and fermenting banana. The beetles were then maintained in the laboratory on standard pinto bean diet in the same way as *C. hemipterus*. Adult beetle lived as long as 6 months under these conditions. Volatiles were collected from *C. lugubris* in the same way as for *C. hemipterus*. The wind tunnel bioassay, as developed for *C. hemipterus*, worked very well for *C. lugubris*. With the latter species, however, it was not necessary to provide "host" volatiles as a pheromone synergist. The beetles responded very well to just the pheromone. The bioassays of beetle-derived preparations used approximately 5 beetle-days of material per test. The chromatographic, spectral, and chemical methods developed for *C. hemipterus* were also used for *C. lugubris*.

As shown in Table XV, the Tenax collections from male beetles were far more attractive than collections from females. That the female-derived preparation attracted any beetles at all was probably due to volatiles from the beetle diet, which was present during volatile collection.

TABLE XIV

*C. hemipterus*: Comparison of Six Binary Tetraene Mixtures with the Standard Synthetic Mixture

| Treatment | Mean Bioassay Count (n = 12) |
|---|---|
| Control | 0.8 a |
| Synthetic mix | 16.4 cd |
| 1 + 2 | 21.0 d |
| 1 + 3 | 1.5 b |

TABLE XIV-continued

C. hemipterus: Comparison of Six Binary Tetraene Mixtures with the Standard Synthetic Mixture

| Treatment | Mean Bioassay Count (n = 12) |
|---|---|
| 1 + 6 | 14.2 c |
| 2 + 3 | 14.4 cd |
| 2 + 6 | 16.2 cd |
| 3 + 6 | 14.7 cd |

Balanced incomplete block experiment (8 treatments, tested 2 at a time). Means followed by the same letter not significantly different (P > 0.05, LSD method). As in Table XIII, tetraene 1 tested at 1.0 ng per test; the others (2, 3, and 6) were tested at 250 pg per test. The synthetic mixture was used at 1.3 ng per test.

TABLE XV

Isolation of Pheromone from Tenax Collections of Volatiles from Carpophilus lugubris[a]

A. Comparison of Collections from Males and Females

| Source of Volatiles | Mean Bioassay Count (n = 7) |
|---|---|
| Male culture | 14.1 |
| Female culture | 1.4 |

B. Fractionation of Tenax Collection from Males on Silica

| | Mean Bioassay Count (n = 4) | |
|---|---|---|
| Fraction | Fraction | Control |
| Hexane | 30.3* | 0.3 |
| 5% Ether in hexane | 0.0 | 0.8 |
| 10% Ether in hexane | 0.3 | 0.5 |
| 50% Ether in hexane | 2.0[b] | 0.5 |
| 10% MeOH in $CH_2Cl$ | 3.8[b] | 0.0 |

C. Fractionation of Hexane Silica Fraction by $AgNO_3$-HPLC

| | Mean Bioassay Count (n = 4) | |
|---|---|---|
| Elution Volume (ml) | Fraction | Control |
| 3.0–4.5 | 0.0 | 0.3 |
| 4.5–5.0 | 0.0 | 0.0 |
| 5.0–5.5 | 0.3 | 0.5 |
| 5.5–6.0 | 42.3* | 0.0 |
| 6.0–6.5 | 12.3* | 0.3 |
| 6.5–7.0 | 4.0* | 0.0 |
| 7.0–7.5 | 0.0 | 0.5 |

[a]Each fraction or extract contained ca. 5 beetle-days of material. No coattractant was added to the treatments. The symbol "*" denotes a statistically significant (P < 0.05) difference from the control.
[b]The slight activity in these fractions was due to components derived from the diet.

Fractionation of the male-derived Tenax collection on silica and subsequent bioassays indicated that the pheromone of *C. lugubris* was very nonpolar (eluting with hexane) and was probably a hydrocarbon.

The hexane fraction from silica was further separated by $AgNO_3$-HPLC. The fractions 5.5-6.5 ml after injection were quite active. The active compounds were retained on the column (column void volume was 3.0 x1), thus there was evidence for the presence of double bonds. In fact, active compounds from *C. hemipterus* had eluted from the $AgNO_3$ column in much the same way.

Comparison of $AgNO_3$ fractions derived from male and female *C. lugubris* by GC revealed one male-specific peak in the active HPLC fraction. This corresponded in retention time to a compound encountered previously in *C. hemipterus* (retention index = 15.15). The compound was identified as structure 6, Table I, based on mass spectrometry, hydrogenation followed by mass spectrometry, and comparison to four candidate synthetic compounds (6, 7, 11, 12, Table I). The natural compound matched structure 6 perfectly with respect to GC retention; $AGNO_3$-HPLC retention; mass spectrum; and number, GC retentions, and mass spectra of hydrogenated derivatives.

*C. lugubris* responded readily to 6 as well as to three of the tetraenes identified previously from *C. hemipterus* (structures 1, 2, and 3). *C. lugubris* did not respond to 5 (Table XVI); thus, *C. lugubris* showed much the same tetraene preference as *C. hemipterus*.

Certain host plant volatiles sometimes synergized the effect of compound 6 on *C. lugubris*. The results are shown in Table XVII. In contrast to *C. hemipterus*, aromatic esters (e.g., benzyl acetate) were effective individually and as synergists. Overall attractiveness could be increased by combining more than one host volatile.

TABLE XVI

Activity of Synthetic Tetraenes for Carpophilus lugubris

| Structure Number | Mean Bioassay Count (n = 4) | |
|---|---|---|
| | Tetraene | Control |
| 1 | 5.8* | 0.3 |
| 2 | 13.8* | 0.0 |
| 3 | 6.5* | 0.3 |
| 5 | 0.3 | 0.3 |
| 6 | 23.8* | 0.0 |

Each tetraene tested at 1 ng per test. No coattractant was added to the treatments. Significant differences between tetraenes and controls are denoted by (*) (P = 0.05)

TABLE XVII

Synergistic Interaction Between Host Plant Volatiles and Pheromones of Carpophilus lugubris

| | Mean Bioassay Count | | |
|---|---|---|---|
| Volatile | Volatile | Pheromone | Volatile + Pheromone |
| Phenylacetaldehyde | 1.1 a | 10.6 b | 11.4 b |
| Apple cider vinegar, ethanol, benzyl acetate | 21.3 a | 6.2 b | 39.5 c |
| Benzyl acetate | 3.0 a | 2.2 a | 8.2 b |
| Ethanol, ethyl acetate, acetaldehyde | 6.6 a | 3.5 a | 16.2 b |
| Methanol, water, propyl acetate, methyl butanoate | 6.5 a | 16.3 b | 29.1 b |

In this experiment, the pheromone was compound 6, Table I, 2 ng. Volatiles were used at a dose of 2 mg and were formulated as 10% solutions or suspensions in mineral oil. In each line, means followed by the same letter do not differ significantly (LSD, P = 0.05)

*C. freemani*

*C. freemani* beetles were field collected at the same location as *G. lugubris*. The beetles were easily reared on the standard pinto bean diet developed for *C. hemipterus*. Volatiles were collected from *C. freemani* onto Tenax in the same way as for *C. hemipterus*. The wind-tunnel bioassay was used for *C. freemani* in the same way as for *C. lugubris*. Host-derived coattractants were not required for excellent bioassay responses; the pheromone alone was sufficient.

Tenax collections from males and females of *C. freemani* were compared by GC after purification on silicic acid. As with *C. hemipterus* and *C. lugubris*, hydrocarbons existed that were present only in the males. The most abundant of these (retention index=12.2) amounted to ca. 50 ng/beetle-day. Another compound (retention index=15.15) was present at 3.0% of the level of the first compound.

Initially, sufficient numbers of beetles were not available for highly replicated, quantitative bioassays; but qualitatively, the beetles responded clearly in the wind tunnel to the hydrocarbon fraction of the Tenax collection and also to AgNO$_3$-HPLC fractions which contained the most abundant male-specific hydrocarbon. The mass spectrum of this compound indicated a molecular weight of 164, corresponding to the molecular formula, $C_{12}H_{20}$, which has three double-bond equivalents. Hydrogenation led to products with a molecular weight of 170. Thus 6 hydrogen atoms were taken up, and the original compound was acyclic. The derivatives with molecular weight 170 corresponded to 2 GC peaks. Two asymmetric centers were probably created during hydrogenation, and the four resulting enantiomers could produce no more than two peaks on an achiral GC column. The intense fragment ion (15% of base peak) at x/z=141 (M-29) in the spectrum of the saturated derivative suggested an ethyl branch. Together, the data suggested 5-ethyl-3-methylnonane as the carbon skeleton. By analogy to the other pheromone compounds, (2E,4E,6E)-5-ethyl-3-methyl-2,4,6-nonatriene (14) was synthesized as a model compound for analytical comparison with the pheromone component. The synthetic and natural compounds were identical in every way.

The minor component (retention index=15.15) was chromatographically and spectroscopically identical to the pheromone of *C. lugubris* and was therefore concluded to be compound 6.

It was eventually possible to rear large numbers of the beetles so that quantitative wind tunnel bioassays could be conducted easily. As shown in Table XVIII, compound 14 was very active in the wind tunnel at a level of ca. 0.6 beetle-days (30 ng). The minor component (6) was also significantly active by itself, although far less active than 14, when tested at the same proportions as emitted by male beetles. However, when 14 and 6 were combined, the response was over 2 times greater than for 14 alone. Furthermore, on an equal weight basis, the combination of 14 and 6 together was equivalent in activity to the natural, beetle-derived pheromone. Thus 14 and 6 together constitute the aggregation pheromone of *C. freemani*.

Although host-derived volatiles are not required for successful wind tunnel bioassays, such volatiles do synergize the activity of the pheromone (Table XIX). Although thorough screens have not been undertaken, it is likely, based on the representative compounds tested, that the same compounds that are effective for *C. hemipterus* will also work for *C. freemani*.

Applications of the Invention

The importance of olfaction in the behavior of insects is well known. Insect-produced volatiles, e.g., pheromones, and host plant odors may facilitate location of conspecifics for mating and orientation to acceptable host plants for feeding and oviposition.

TABLE XVIII

| C. freemani: Bioassay Activity of Synthetic Hydrocarbons | |
|---|---|
| A. Activity of compounds 14 and 6, alone and in combination. | |
| Treatment | Mean Bioassay Count (n = 12) |
| Control | 0.0 d |
| Compound 14 (30 ng) | 46.0 b |
| Compound 6 (1 ng) | 2.8 c |
| Compounds 14 (30 ng) and 6 (1 ng) | 103.8 a |
| B. Comparison of beetle-derived pheromone and mixture of 14 and 6 | |
| Treatment | Mean bioassay count (n = 8) |
| Control | 0.0 b |
| Beetle-derived pheromone | 23.6 a |
| Compounds 14 (30 ng) + 6 (1 ng) | 26.3 a |

Three-minute tests. Balanced incomplete block experiments; in each experiment, means followed by the same letter not significantly different (LSD, 0.05). In part B, the natural ratio of compounds 14 and 6 in the beetle-derived pheromone is 30:1, and the amounts of these compounds per test were the same as for the synthetic compounds. The beetle-derived sample was from a Tenax collection and had been partially purified on silicic acid (elution with hexane).

TABLE XIX

| Synergistic Interaction between Host Plant Volatiles and Pheromone of C. freemani | | |
|---|---|---|
| | Mean Bioassay Count | |
| Volatile | Volatile | Compound 14 | Volatile + Compound 14 |
| Propyl acetate | 0.9 a | 12.6 b | 38.2 c |
| Ethanol | 1.4 a | 30.5 b | 67.7 c |
| Valeric acid | 0.1 a | 10.4 b | 21.6 c |

Compound 14 was used at 40 ng per test. Volatiles were used at 2 mg per test, as 10% solutions or suspensions in mineral oil. In each line, means followed by different letters are significantly different (LSD, P = 0.05).

Pheromones that are attractive alone may have their activity enhanced or synergized by host plant odors which show little attraction when presented alone. The pheromones of this invention may be used as a crude extract of *Carpophilus* sp. beetles or in substantially purified form either isolated from the natural source or chemically synthesized. As a practical matter, it is expected that substantially pure pheromone will be formulated with an inert carrier for use as an insect attractant composition. Alternatively, the pheromone composition ray be further formulated with other pheromones or synergists; insecticides may also be included in the attractant composition to effect insect control.

With the identification of the *Carpophilus* sp. beetle pheromones and synergists therefor, a tool is available to monitor beetle populations for directing insecticide applications and evaluating control measures. The synergized pheromones may also be potentially used to control pest populations by employing large numbers of traps (trap-out strategy).

A synergist is herein defined as a material that enhances the activity of other materials, so that the overall activity of the mixture be is greater than the sum of the individual components. An effective synergist for an attractant pheromone facilitates insect population monitoring and control by increasing both the level and longevity of pheromone attractiveness. The compounds useful as synergists are comparatively inexpensive, and thereby enhance the cost effectiveness of insect control using pheromones.

The potency of these synergized pheromone compositions dictates that they be applied in conjunction with a suitable inert carrier or vehicle as known in the art. Of particular interest are those which are agronomically acceptable. Alcohols, hydrocarbons, halogenated hydrocarbons, glycols, ketones, esters, and aqueous mixtures, and solid carriers such as clays, cellulose, rubber, or synthetic polymers are illustrative of suitable carriers. The synergized pheromone compositions may be used in a number of ways, e.g., in combination with pesticides to kill the insects or in traps to monitor population changes or to kill insects in the traps. Other formulations and methods of use will be obvious to skilled artisans.

Formulation is herein defined as a physical combination of at least one aggregation pheromone with one or more materials selected from the group of other pheromones, synergistic materials, insecticides, and inert carriers.

The synergized pheromone compositions encompassed herein are effective in attracting a variety of organisms. Without desiring to be limited thereto, pests of particular interest known to be susceptible to treatment are agronomically important insects, especially the nitidulid species C. hemipterus, C. lugubris, and C. freemani.

The insect pheromones of this invention are represented by the general structure:

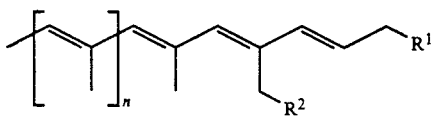

where $R^1$ and $R^2$ are independently selected from the group consisting of hydrogen and lower alkyl, and n is zero or one. Compounds 1, 2, 3, 6, 11, and 14 (Table I) are examples of the general structure. It will be noted that not all examples are active for each species of nitidulid. It will be obvious to those skilled in the art to choose a compound that attracts the desired insect and an amount of the pheromone that will be effective.

The arrangement of the double bonds must be in the "E" configuration, as illustrated in the general formula. Compounds with Z configured double bonds are not effective. See, for example, compounds 8 and 9 in Table I.

It will be obvious to skilled workers in the insect pheromone field that the ratio and absolute amounts of active ingredients may be varied depending upon environmental conditions such as temperature, humidity, wind velocity, and insect population.

The following examples are intended only to further illustrate the invention and are not intended to limit the scope of the invention which is defined by the claims.

EXAMPLE 1

BIOASSAY METHOD

All bioassays were conducted in a wind-tunnel olfactometer constructed of Plexiglas 0.60×0.60 m in cross section and 1.35 m long. The floor was plywood, which was rough enough in texture to allow any beetles that had fallen on their backs to right themselves. The ends were covered with 30-mesh steel screen. An electric fan was connected by a duct to the upwind end; air was drawn from the room and forced through the wind tunnel. Laminar flow was achieved by passing the air through several layers of cheesecloth mounted outside the upwind screen, as described by Baker and Linn (1984). The linear air flow rate was 0.3 x/sec. The temperature was kept at 27°; the relative humidity was not controlled but was in the range of 30-40%. The wind tunnel was lighted from above with four 40-watt fluorescent tubes.

About 24 hr before bioassays were to begin, cultures containing a total of 200-400 beetles about 1-3 weeks old (except for C. lugubris which were as old as 6 mo) were placed in a fume hood for 8 hr, during which the diet medium dried down to about 75% of its original volume. The beetles were then transferred to the wind tunnel and kept without food for an additional 16 hr. The hood-drying step was omitted for C. freemani. Lights and air flow were left off during this time but were turned on before beginning bioassays. Beetles were never observed to fly to a bait unless they had been starved for a number of hours. For good responsiveness, the beetles had to have been without food but not unduly stressed. With the above procedure, the beetles appeared healthy and usually began to respond to attractive baits within 1 hr of turning on the wind-tunnel lights and fan. Once the beetles were ready, as many as 30-50 three-minute tests could be run in the course of a day.

Test baits were suspended from a horizontal wire 0.4 m above the floor of the wind tunnel, perpendicular to the air flow and 0.2 m from the unwind screen. Baits were always tested in pairs, separated by 0.3 m. Extracts or chromatographic fractions to be used as baits were applied to 7-cm circles of filter paper which were folded into quarters and secured with a paper clip. Concentrations of test solutions were adjusted so that the application volume was in the range of 10-30 $\mu$l. Because of the location of the baits, beetles could reach them only by flying. The test period was 3 min; during this time the number of beetles landing on each bait was recorded. Tests were always replicated and each bait was tested in both positions, so that any position effects would not bias comparisons of treatments. Tests were separated in time by 2-5 min.

Bioassays were interpreted in terms of the mean counts of responding beetles. However, the counts for a particular treatment varied from day to day and even from hour to hour, depending on such factors as the number of beetles in the wind tunnel, their health, and the length of time that they had been starved prior to testing. To control for this variability, treatments are always tested two at a time in the wind tunnel. Thus, even if the level of responsiveness in the wind tunnel was low at the time of the test, both treatments showed decreased counts. Relative to each other, the treatments retained proper relationships. Ratios of counts between treatments have remained quite constant over time. Efforts were made to keep the level of beetle activity in the wind tunnel fairly constant from day to day, but comparison of mean counts is only justified within an experiment (not between experiments), and it is usually the ratios of means which ar of greatest usefulness.

EXAMPLE 2

EXTRACTION

Beetles to be extracted were immobilized over ice and separated by sex within 7 days of emergence; then they were returned to rearing cups until extraction. The 30-ml plastic rearing cups normally contained up to 100 beetles and ca. 10 ml of the pinto bean rearing medium (diet).

As a typical example of an extraction, 300 male beetles, 9–12 days old, and the diet medium from the 4 rearing cups which held these were soaked in 100 ml of methylene chloride for 15 min. The extraction was repeated twice more, and the combined extracts were filtered and dried over sodium sulfate. The extract was reduced in volume to 10 ml by rotary evaporation. Concentrations were calculated as beetle equivalents (the amount of pheromone extractable from 1 beetle) per ml, based on counts of beetles and extract volumes.

EXAMPLE 3

VOLATILE COLLECTION

A 50-ml filtering flask was fitted with a cork into which a Tenax trap was inserted. The Tenax trap was prepared from a 10 cm ×0.5 cm (ID) piece of soft glass tubing. A piece of brass screen (100 mesh) was sealed into the end by heating. The tube was filled to a depth of 0.5 cm with Tenax porous polymer (60/80 mesh, Alltech, Deerfield, IL) which had been cleaned by extraction with hexane in a Soxhlet apparatus. The Tenax was held in place by a plug of glass wool. About 15 ml of pinto bean diet were placed into the flask, and the tip of the Tenax trap was adjusted to about 1 cm above the diet. A vacuum was applied to the Tenax trap so that volatiles within the flask were drawn into the trap. A second Tenax trap was attached to the side arm of the flask to clean the air drawn into the flask. This connection was made with "Teflon" tubing. Approximately 100 male beetles were added to the flask, and the air flow through the flask was adjusted to 50 ml/ min. The flask was kept in an incubator at 27° and 40% relative humidity. At this humidity the diet dried out slowly over a week: with the diet in this condition, the beetles remained active and healthy, but the growth of mold was retarded. The beetles received 14 hr of light each day. Eighteen such flasks were operated in the incubator at one time. Pheromone collections were quantified in terms of beetle-days, defined as the average amount of pheromone collected from one beetle in one day. Volatile collections were also made from female beetles and from diet medium without beetles.

To extract volatiles from the Tenax traps, each trap was rinsed three times with 200 μl hexane. Before returning the trap to its flask, air was passed through the trap to evaporate residual solvent. Traps were rinsed every 2 or 3 days. The extracts were set aside for chromatography.

EXAMPLE 4

CHROMATOGRAPHY

Column chromatography on silicic acid was used for all initial purifications. Columns were usually 5 cm by 0.5 cm, and these were adequate for extracts with 100 beetle equivalents, including diet medium. Before chromatography the methylene chloride be was carefully removed from these extracts under nitrogen, and the samples were taken up in hexane. Columns were eluted with 2 column volumes each (2 ml) with these solvents: hexane; 5%, 10%, and 50% ether in hexane; and 10% methanol in methylene chloride. Each solvent was collected as a separate fraction. Larger columns were used for extracts with greater numbers of equivalents.

The rinses from the Tenax traps were also applied to these silicic acid columns; a collection 3000 beetle-days in size did not overload a 5 cm ×0.5 cm column.

Silicic acid containing 25% AgNO₃ was also used as a packing in open columns (5 cm ×0.5 cm). The samples were applied in hexane and the columns eluted with hexane; 5%, 10%, and 25% ether in hexane; and finally, with ether.

All chromatographic separations and syntheses were monitored by gas chromatography (GC) using a Varian 3700 gas chromatograph. It was equipped with flame ionization detector, splitless injector for capillary columns, effluent splitter for preparative GC on a packed column, and effluent collector (Brownlee and Silverstein, 1968). Two columns were used: The first was a 15 m ×0.25 mm (ID) DB-1 capillary with a 1.0 μm film thickness (J & W Scientific, Folsom, CA). For many samples, this column was programmed from 100° to 200° at 10° per min, although cooler starting temperatures or hotter final temperatures were sometimes required. Beetle-derived samples were usually concentrated by 20–100 times by evaporation under $N_2$, so that the 1–2 μl injections would have enough material to be easily detected (>1 ng per component). The other column, used for preparative GC, was a 2 m ×2 mm (ID) glass column, packed with 3% OV-101 on Chromosorb WHP 100/200 (Alltech). The gas chromatograph was interfaced to a Hewlett-Packard 3396A integrator.

Retention indices (I) relative to n-alkane standards were determined for the male-specific hydrocarbons. The DB-1 column was programmed from 100° to 200° at 10° per min, and the retention indices calculated by linear interpolation (Poole and Schuette, 1984, pp. 23–25).

High performance liquid chromatography (HPlC) was conducted isocratically using a Waters Associates model 6000 pump and R401 refractometer detector. Two columns were used. The first was a 30 cm ×0.75 cm (ID) PLGEL 50A 10 μm size-exclusion column (Polymer laboratories, Shropshire, UK), and it was eluted with hexane. The other column was a 25 cm ×0.46 cm (ID) Lichrosorb Si60 silica column (5 μm particle size) (Alltech), coated with AgNO₃ as described by Heath and Sonnet (1980). This column was eluted with 25% toluene in hexane. The void volumes for the two columns were estimated to be 8 and 3.5 ml, respectively. The beetle-derived samples were not concentrated enough to be detected by the refractometer. Effluent was collected as 1-ml or 0.5-ml fractions, which were later analyzed by GC and bioassayed.

EXAMPLE 5

SPECTRA

Mass spectra were obtained on a Finnigan 4535 quadrupole mass spectrometer. Sample introduction was always by GC (DB-1 capillary). An ionizing potential of 70 eV was used for electron impact spectra. NMR proton spectra were obtained on a Bruker 300 mHz instrument. Samples were dissolved in deuterobenzene and shifts were calculated relative to tetramethylsilane. Further experimental details are given with results. Ultraviolet spectra were taken with a Perkin Elmer (Norwalk, CT) Lambda 4B high performance UV spectro-photometer. The solvent was hexane.

EXAMPLE 6

HYDROGENATION OF C-13 COMPOUND

Saturated derivatives of male-derived hydrocarbons were prepared by the method of Parliment (1973), except that Methylene chloride was used as the solvent. Palladium (10%) on carbon was used as the catalyst in the initial reactions, but PtO$_2$ was later found to be preferable because it caused less formation of cyclic side be products. The saturated derivatives were analyzed by mass spectrometry to gain structural information about the carbon skeletons.

By GC, hydrogenation of the major, 13-carbon compound over Pd produced at least 12 distinct compounds. The key products had molecular weights of 184; the uptake of 8 hydrogens indicated the existence of 4 double bonds and no rings (if no triple bonds). However, other products had molecular weights of 182 and would not hydrogenate further. Apparently, cyclic rearrangement competed with simple hydrogenation. PtO$_2$ as catalyst gave a greater proportion of the acyclic product, which was more useful for structure elucidation.

Mass chromatograms were prepared for the ions in the series, $C_nH_{2n+1}^+$, n=4, ..., 12. These fragments, m/z=57, 71, 85, ..., 169, were the dominant features for the acyclic products but were nearly absent from the cyclic products (which had $C_nH_{2n-1}^+$ as the primary series). Based on the mass chromatograms, there were four acyclic products (two of which were poorly resolved on the DB-1 capillary), and these all had nearly identical mass spectra.

The intensities of the $C_nH_{2n+1}$ peaks, especially those of higher mass, give structural information about branched alkanes (Nelson, 1978). These tend to fragment at branch points, with the secondary carbonium ion retaining the charge. Compared with the spectrum for tridecane, the peaks at 155, 141, 113, and 99 were relatively enhanced, while those at 127 and 85 were relatively suppressed. These data suggested that the saturated derivative was 3,5,7 -trimethyldecane.

3,5,7-Trimethyldecane possesses three asymmetric centers. If the original compound had double bonds involving the 3, 5, and 7 positions, then catalytic hydrogenation would create these asymmetric centers without stereoselectivity. The resulting eight optical isomers would produce at most 4 GC peaks on an achiral column, which is what we observed.

EXAMPLE 7

UV SPECTRUM OF C-13 COMPOUND

The UV spectrum possessed a maximum at 287 nm ($\epsilon = 2.2 \times 10^4$) and another at 223 nm ($\epsilon = 1.0 \times 10^4$). The maximum at the longer wavelength suggested that three or four double bonds were in conjugation, but because steric and other factors can affect UV absorbance (Silverstein and Bassler, 1967), the exact number of conjugated double bonds was ambiguous.

EXAMPLE 8

NMR SPECTRUM OF C-13 COMPOUND

The NMR spectrum provided important structural information, but handling the samples proved to be difficult. The initial NMR sample of about 20 μg was prepared by preparative GC. The purity of this sample was only 72% by capillary GC, primarily because the target compound rearranged or decomposed to a significant extent on the preparative GC column. Nevertheless, the largest impurity was only 7% of the sample, so useful NMR data could be obtained. This sample was contained in a capillary NMR tube and was scanned 30,000 times. A subsequent NMR sample, containing about 30 μg, was prepared by HPLC on the size-exclusion column. After evaporating the hexane and adding deuterobenzene, the sample was 90% pure by capillary GC. This sample was held in a standard (5 mm) tube, and 3200 scans provided a good-quality spectrum.

The spectra were difficult to interpret because the unknown compound rearranged, polymerized, or both during acquisition of the spectra (in the latter sample, totally). Peaks belonging to the original compound were differentiated from those due to decomposition by observing changes in the spectra over time. At first, no peaks were present in the region 0.8–1.4 ppm; but over time, peaks in this area grew to become the dominant spectral features. Nevertheless, both NMR samples produced identical spectra when the artifact peaks were ignored. The observed resonances were: 6.25 (1H, dq, J=15.4, 2), 6.03 (2H, br s), 5.63 (1H, dq, J=15.4, 6.7), 5.53 (1H, qq, J=6.7, 1), 2.00 (3H, br s), 1.98 (3H, br s), 1.74 (3H, br s), 1.73 (3H, d [half concealed], J=6.7), and 1.64 (3H, d, J=6.6). All the resonances appeared to represent either olefinic protons or olefinic methyl groups. The data suggested that the compound was 3,5,7-trimethyl-2,4,6,8-decatetraene. The double bond at the 8 position had the (E) configuration because of the large coupling constant (J=15.4 Hz) between the olefinic protons, but the configurations at the three trisubstituted double bonds were not determined.

EXAMPLE 9

(1-METHYL-2(E)-BUTENYL)TRIPHENYLPHOSPHONIUM BROMIDE (COMPOUND 24)

In this and following synthesis examples the compounds and reagents for chemical synthesis were obtained from Aldrich Chemical Co. (Milwaukee, WI) and were used as received. Solvents were dried over 4A molecular sieves, except ether, which was dried over sodium metal.

Compound 24 was prepared from triphenylphosphine (Aldrich) and 4-bromo-2-pentene which was a previously known compound (Mulliken et al., 1935).

Triphenylphosphine (3.1 g, 0.012 mole) and 4-bromo-2(E)-pentene (1.7 g, 0.011 mole) were added to 40 ml dry (molecular sieve) acetonitrile and refluxed for 6 hr. The solvent was removed by rotary evaporation, and the sticky product was washed three times with dry ether. Further traces of ether were removed under rotary evaporation and the product was placed in a vacuum desiccator for 2 hr, where it became a friable white solid. Alternatively, the salt crystallized after repeated (>20) washings with dry ether, but the method using the vacuum desiccator was quicker and provided an acceptable reagent for the Wittig reaction.

EXAMPLE 10

(2E, 4E, 6E, 8E)-3,5,7-TRIMETHYL-2,4,6,8-DECATETRAENE (COMPOUND 1)

(1-Methyl-2(E)-butenyl)triphenylphosphonium bromide from Example 9 (0.62 g, 0.0015 mole) was added to a dry flask with 5 ml tetrahydrofuran. The flask was equipped with magnetic stirrer and septum; the reaction was carried out under nitrogen. The salt did not dissolve completely but became a sticky suspension. The mixture was cooled over ice, and butyllithium (2.5 M in hexane) was added dropwise, with stirring, until the color change became permanent; then an additional 0.0015 mole was added. The solid in the flask dissolved as it was converted to the ylide. One hundred milligrams of (2E,4E)-2,4-dimethyl-2,4hexadienal (0.0008 mole), compound 15, a previously known compound (Patel and Pattenden, 1985), was added to the Wittig reagent, and the mixture was allowed to warm to room temperature. The mixture was stirred for 2 hr, and it was again cooled over ice. Water was added dropwise until the red color of the solution had disappeared, and ca. 2 ml more water was added. The mixture was diluted with hexane and the organic layer dried over sodium sulfate. The solvent was removed and the product passed through a silica column with hexane. By capillary GC the product was 61% the (E,E,E,E) isomer, ca. 31% the (E,E,Z,E) isomer, and ca. 8% by-products, after clean-up on silica. Further purification on the AgNO$_3$ HPLC column yielded the (E,E,E,E) isomer in >97% purity.

The (E,E,Z,E) isomer was recognized by its thermal lability. By GC on DB-1 (100–200° at 10°/min), the (E,E,Z,E) isomer produced a rearrangement peak at 3.99, a sharp peak at 5.47, and a broad hump between these peaks. The initial peak could be eliminated by setting the injector temperature at 100°, and the hump (which indicated on-column thermal rearrangement) could be eliminated by using a thinner film column (0.25 µm vs. 1.0 µm), allowing the compound to elute at a cooler temperature (ca 115 Vs. 155°).

EXAMPLE 11

(1-METHYL-2(e)-PENTENYL)TRIPHENYLPHOS-PHONIUM BROMIDE (COMPOUND 25)

The compound was prepared from triphenylphosphine and 2-bromo -3(E)-hexene, a compound which was reported previously (Bianchini and Guillemonat, 1968). Triphenylphosphine (1.6 g, 0.0061 mole) and 2-bromo-3(E)-hexene (1.0 g, 0.0061 mole) were added to 10 rl dry acetonitrile and refluxed for 6 hr. The solvent was removed by rotary evaporation. The thick, sticky, liquid product was stirred with dry ether 4 times, with the ether being decanted. After further traces of ether were removed by rotary evaporation, the protect was placed in a vacuum desiccator for 6 hr, where the product became a friable white solid (1.6 g, 61%).

EXAMPLE 12

(2E,4E,6E,8E)-3,5,7-TRIMETHYL-2,4,6,8-UNDECATETRAENE (COMPOUND 2)

(1-Methyl-2(E)-pentenyl)triphenylphosphonium bromide (0.40 g, 0.0009 mole), from Example 11, was added to a flask with 2 ml dry tetrahydrofuran. The reaction was run under nitrogen, and the flask was equipped with a magnetic stirrer. The mixture was cooled over ice, and butyllithium (2.5 m in hexane) was added dropwise until the color change became permanent; then an additional 0.4 x1 (0.001 role) was added. After 5 min, 100 rg (0.0008 mole) of (2E,4E)-2,4-dixethyl-2,4-hexadienal (15) was added. The mixture was warmed to room temperature, stirred for 2 hr, then cooled over ice again. Water (1 ml) and pentane (3 ml) were added. The aqueous layer was washed twice with 2 rl pentane. The combined organic layers were washed three times with water and dried over Na$_2$SO$_4$. After the product was passed through a silica column with hexane, both the (E,E,E,E) and (E,E,Z,E) isomers were present (47% and ca. 40%, respectively, by GC). The isomers were resolved by HPLC on the silver-nitrate column, as described in Example 10.

EXAMPLE 13

FIELD RESPONSE OF *C. lugubris* TOWARD COMPOUND 6 AND WHOLE WHEAT DOUGH

Traps were baited with: (1) 300 µg of Compound 6 (applied to a red rubber septum with 300 µl of xethylene chloride); (2) ca. 20 ml of whole wheat dough (which had been inoculated with baker's yeast); or (3) a combination of these two baits. Control traps were not baited. The trap design did not allow the captured beetles to contact the bait. The traps were hung 1–1.5 m above the ground in an oak woods near Bath, Illinois. They were placed in pairs (with ca. 1 m separation between traps), and the pairs of traps were separated by at least 20 m. A balanced incomplete block design was used. Numbers of beetles captured were recorded after 3 days.

The synergistic interaction between the pheromone and a food-type bait was more pronounced in the field (Table XX, below) than in the laboratory wind tunnel (Table XVII). Although the pheromone by itself was not significantly more attractive than the controls, the response to the combination of the pheromone and whole wheat dough was greater than 20-fold the response to the wheat dough alone. The field experiment emphasizes the practical importance of combining pheromones with host volatiles for greatest effectiveness under natural conditions.

It is understood that the foregoing detailed description is given merely by way of illustration and that modification and variations may be made therein without departing from the spirit and scope of the invention.

TABLE XX

Field Response of *C. lugubris* Toward Compound 6

| Trap Bait | Mean Trap Catch (n = 6) |
|---|---|
| Control | 0.0 a |
| Whole wheat dough | 9.1 b |
| Compound 6 | 0.8 a |
| Whole wheat dough + compound 6 | 218.3 c |

Means followed by the same letter were not significantly different (LSD, 0.05).

REFERENCES

Alm, S. R., F. R. Hall, T. L. Ladd, Jr., and R. N. Williams. 1985. A chemical attractant for *Glischrochilus quadrisignatus* (Coleoptera: Nitidulidae). J. Econ. Entomol. 78: 839–843.

Alm, S. R., F. R. Hall, T. P. McGovern, and R. N. Williams. 1986. Attraction of *Glischrochilus quadrisignatus* (Coleoptera: Nitidulidae) to semiochemicals: butyl acetate and propyl propionate. J. Econ. Entomol. 79: 654–658.

Appel, D. N. 1986. Occurrence of nitidulid beetles (Coleoptera: Nitidulidae) in Texas oak wilt centers. J. Econ. Entomol. 79: 1276–1279.

Baker, T. C., and C. E. Linn, Jr. 1984. Wind tunnels in pheromone research. In Techniques in Pheromone Research, H. E. Hummell and T. A. Miller, eds., Springer-Verlag, New York, 464 pp.

Bianchini, J.-P., and A. Guillemonat. 1968. Action des acides chlorhydrique et bromhydrique sur les carbures alleniques. Bull. Soc. Chim. Fr. 1968: 2120–2123.

Borden, J. H. 1984. In Insect Communication, T. lewis, ed., Academic Press, New York, p. 123.

Boutagy, J., and R. Thomas. 1974. Olefin synthesis with organic phosphonate carbanions. Chem. Rev. 74: 87–99.

Brooks, L. A., and H. R. Snyder. 1955. 3-Penten-2-ol. Org. Synth., Coll. Vol. 3: 696–698.

Brownlee, R. G., and R. M. Silverstein. 1968. A micropreparative gas chromatograph and a modified carbon skeleton determinator. Anal. Chem. 40: 2077–2079.

Connell, W. A. 1956. Nitidulidae of Delaware. Univ. of Delaware Agric. Exper. Sta. Tech. Bull. #318, 67 pp.

Connell, W. A. 1975. Hosts of *Carpophilus dimidiatus*. J. Econ. Entomol. 68: 279–280.

Dess, D. B., and J. C. Martin. 1983. Readily accessible 12-I-5 oxidant for the conversion of primary and secondary alcohols to aldehydes and ketones. J. Org. Chem. 48: 4155–4156.

Dorsey, C. K., F. F. Jewell, J. G. Leach, and R. P. True. 1953. Experimental transmission of oak wilt by four species of Nitidulidae Plant Dis. Rep. 37: 419–420.

Dorsey, C. K., and J. G. Leach. 1956. The bionomics of certain insects associated with oak wilt with particular reference to the Nitidulidae. J. Econ. Entomol. 49: 219–230.

Dowd, P. F. 1987. A labor saving method for rearing the driedfruit beetle (Coleoptera: Nitidulidae) on pinto bean-based diet. J. Econ. Entomol. 80: 1351–1353.

Gallagher, G., Jr., and R. L. Webb. 1974. Tetrasubstituted acrylates: the Wittig-Horner reaction of ketones with triethyl 2-phosphonopropionate. Synthesis 1974, No. 2: 122–124.

Heath, R. R., and P. E. Sonnet. 1980. Technique for in situ coating of Ag+ onto silica gel in HPLC columns for the separation of geometrical isomers. J. Liq. Chromatog. 3: 1129–1135.

Hinton, H. E. 1945. A Monograph of the Beetles Associated with Stored Products. Jarrold and Sons, Norwich, U.K., 443 pp.

Luckman, W. H., and E. T. Hibbs. 1959. Present status in the North Central states of some nitidulids known to damage sweet corn. Proc. North Central Br. Entomol. Soc. Am. 14: 81–82.

Moller, W. J., J. E. DeVay, and P. A. Backman. 1969. Effect of some ecological factors on Ceratocystis canker in stone fruits. Phytopathology 59: 938–942.

Mori, K. 1976. Synthesis of optically active forms of ipsenol, the pheromone of IPs bark beetles. Tetrahedron 32: 1101–1106.

Mulliken, S. P., R. L. Wakeman, and H. T. Gerry. 1935. The preparation of certain alkenes, alkadienes and alkynes. J. Am. Chem. Soc. 57: 1605–1607.

Neel, W. W., B. D. Glick, L. L. May, and R. P. True. 1967. Attractiveness to Nitidulidae (Coleoptera) of natural attractants of tree and fungus origin supplemented with vinegar and water in an Appalachian hardwood forest. J. Econ. Entomol. 60: 1104–1109.

Nelson, D. R. 1978. Long-chain methyl-branched hydrocarbons: occurrence, biosynthesis and function. Adv. Insect Physiol. 13: 1–33.

Noller, C. R., and R. Dinsmore. 1943. Isobutyl bromide. Org. Synth., Coll. Vbl. 2: 358–360.

Norris, D. M. 1953. Insect transmission of oak wilt in Iowa. Plant Dis. Rep. 37: 417–418.

Obenauf, G., H. Black, C. Knight, and K. Husbands. 1976. Monitoring insect populations in fig orchards. Proc. Calif. Fig Inst. Res. 1976: 61–94.

Parliment, T. H. 1973. Convenient technique for microhydrogenation. Microchem. J. 18: 613–616.

Parsons, C. T. 1943. A revision of the nearctic Nitidulidae (Coleoptera) Harvard Univ. Museum Comp. Zool. Bull. 92: 121–278.

Patel, P., and G. Pattenden. 1985. Natural polyene a-pyrones. Total synthesis of citreomontanin from *Penicillium pedomontanum*. Tetrahedron Lett. 26: 4789–4792.

Pfeiffer, D. G., and R. C. Axtell. 1980. Coleoptera of poultry manure in caged-layer houses in North Carolina. Environ. Entcmol. 9: 21–28.

Phillips, J. K., and W. E. Burkholder. 1981. Evidence for a male-produced aggregation pheromone in the rice weevil. J. Econ. Entomol. 74: 539–542.

Poole, C. F., and S. A. Schuette. 1984. Contemporary Practice of Chromatography. Elsevier, Amsterdam, 708 pp.

Sanford, J. W. 1958. Observations on the biology and control of the dusky sap beetle, *Carpophilus lugubris* Murray, infesting sweet corn in Illinois. Univ. of Illinois, Urbana, 54 pp.

Sanford, J. W., and W. H. Luckman. 1963. Observations on the biology and control of the dusky sap beetle in Illinois. Proc. North Central Br. Entomol. Soc. Am. 18: 39–43.

Silverstein, R. M., and G. C. Bassler. 1967. Spectrometric Identification of Organic Compounds. John Wiley and Sons, New York, 256 pp.

Smilanick, J. M., and L. E. Ehler. 1976. An analysis of the insect component of field-collected, infested figs for 1975. Proc. Calif. Fig Inst. Res. Meet., 1976: 27–41.

Smilanick, J. M., L. E. Ehler, and M. C. Birch. 1978. Attraction of *Carpophilus* spp. (Coleoptera: Nitidulidae) to volatile compounds present in figs. J. Chem. Ecol. 4: 701–707.

Sonnet, P. E. 1974. cis-Olefins from the Wittig reaction. Org. Prep. Proc. Int. 6: 269–273.

Tamaki, G., L. Fox, and P. Featherston. 1982. Laboratory biology of the dusky sap beetle and field interaction with the corn earworm in ears of sweet corn. J. Entomol. Soc. Brit. Columbia 79: 3–8.

Wicklow, D. T., H. R. Burmeister, P. F. Dowd, and M. G. Smart. 1988. NC-151 progress report for 1987, pp. 31–32. In NC-151, 1987: Annual Progress Reports from Participating Laboratories.

We claim:

1. A substantially pure hydrocarbon or a substantially pure mixtures of hydrocarbons having the structure:

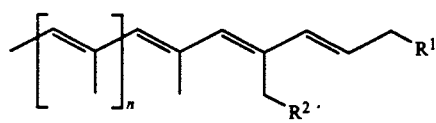

wherein $R^1$ and $R^2$ are independently selected from the group consisting of hydrogen and lower alkyl, and n is zero or one.

2. A compound as described in claim 1 wherein $R^1$ is hydrogen, $R^2$ is methyl, and n is one.

3. A compound as described in claim 1 wherein $R^1$ is methyl, $R^2$ is methyl, and n is one.

4. A compound as described in claim 1 wherein $R^1$ is ethyl, $R^2$ is hydrogen, and n is one.

5. A compound as described in claim 1 wherein $R^1$ is methyl, $R^2$ is methyl, and n is zero.

* * * * *